US00PP37128P2

(12) United States Plant Patent
Bourne

(10) Patent No.: US PP37,128 P2
(45) Date of Patent: Dec. 9, 2025

(54) GRAPEVINE PLANT NAMED 'SV34-130-197'

(50) Latin Name: *Vitis vinifera*
Varietal Denomination: SV34-130-197

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,683

(22) Filed: Jul. 16, 2025

Related U.S. Application Data

(60) Provisional application No. 63/732,295, filed on Jul. 31, 2024.

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./205
CPC ..... A01H 6/88; A01H 5/08
See application file for complete search history.

*Primary Examiner* — Keith O. Robinson
(74) *Attorney, Agent, or Firm* — Erie C. Cole; Baker Manock & Jense

(57) ABSTRACT

A new and distinct variety of grapevine plant named 'SV34-130-197' particularly characterized by its cylindrical-shaped, very crisp berries that have a muscat flavor and which ripen in early July in the McFarland, California area.

5 Drawing Sheets

STATEMENT OF ANY FEDERALLY-SPONSORED RESEARCH AND DEVELOPMENT

The present invention is not subject of Federally-sponsored research or development.

Latin name of the genus and species of the plant claimed: The plant claimed relates to a new and distinct variety of *Vitis vinifera*.

Variety denomination: The plant claimed shall be known as 'SV34-130-197'.

BACKGROUND OF THE INVENTION

The present invention comprises a new and distinct cultivar of grapevine botanically known as *Vitis vinifera* and hereinafter referred to as grapevine named 'SV34-130-197'. As used herein, 'grapevine' refers to all plant parts including, vines, canes, tendrils, leaves, fruit and roots of grapevine named 'SV34-130-197'. Grapevine named 'SV34-130-197' is the result of an effort to produce an early-ripening, white seedless table grape with fruit characteristics superior to currently available cultivar 'Sugraone' (unpatented). This new cultivar originated from a cross conducted in May 2013 near McFarland, California between female parent grapevine plant selection 'SV16-72-83' (unpatented) and male parent grapevine 'SV21-66-158' (U.S. Plant Pat. No. 24,510). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in November of 2014 and grown in the greenhouse at 29° C. with 12 hours illumination under high pressure sodium vapor lamps. The seedling population of 132 plants was planted in the field in the spring of 2014 near Delano, California. The new grapevine was selected from this seedling population on Jul. 9, 2016. It was then propagated by cuttings and grafted to 'Freedom' (unpatented) rootstock in 2017. The present invention has been found to retain its distinctive characteristics through two successive asexual propagations in 2017 and 2021 near Delano, California.

Grapevine named 'SV34-130-197' differs from its female parent grapevine 'SV16-72-83' (unpatented) by having fruit that ripens in early July when grown near Delano, California while 'SV16-72-83' fruit ripens in September when grown near Delano, California. Grapevine named 'SV34-130-197' produces fruit with small, soft seed traces that are not noticeable when eating while the seed traces of grapevine 'SV16-72-83' (unpatented) are large and partially lignified.

Grapevine named 'SV34-130-197' differs from its male parent 'SV21-66-158' (U.S. Plant Pat. No. 24,510) in that grapevine named 'SV34-130-197' produces looser and less compact fruit clusters than 'SV21-66-158' (U.S. Plant Pat. No. 24,510).

Grapevine named 'SV34-130-197' most closely resembles commercially available grapevine 'SV21-66-226' (U.S. Plant Pat. No. 24,531) but may be distinguished by its smaller berry size and its less compact fruit clusters.

SUMMARY OF THE INVENTION

The following are the most outstanding and distinguishing characteristics of the ripe fruit of this new variety when grown under normal horticultural practices near McFarland, California:

a. Cylindrical shaped, sweet berries with muscat flavor.
b. Very crisp berry texture; and
c. Very heavy fruit production.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from a plant approximately 7 years old, grown in a field near McFarland, California in 2024.

DETAILED BOTANICAL DESCRIPTION

Figure 1:
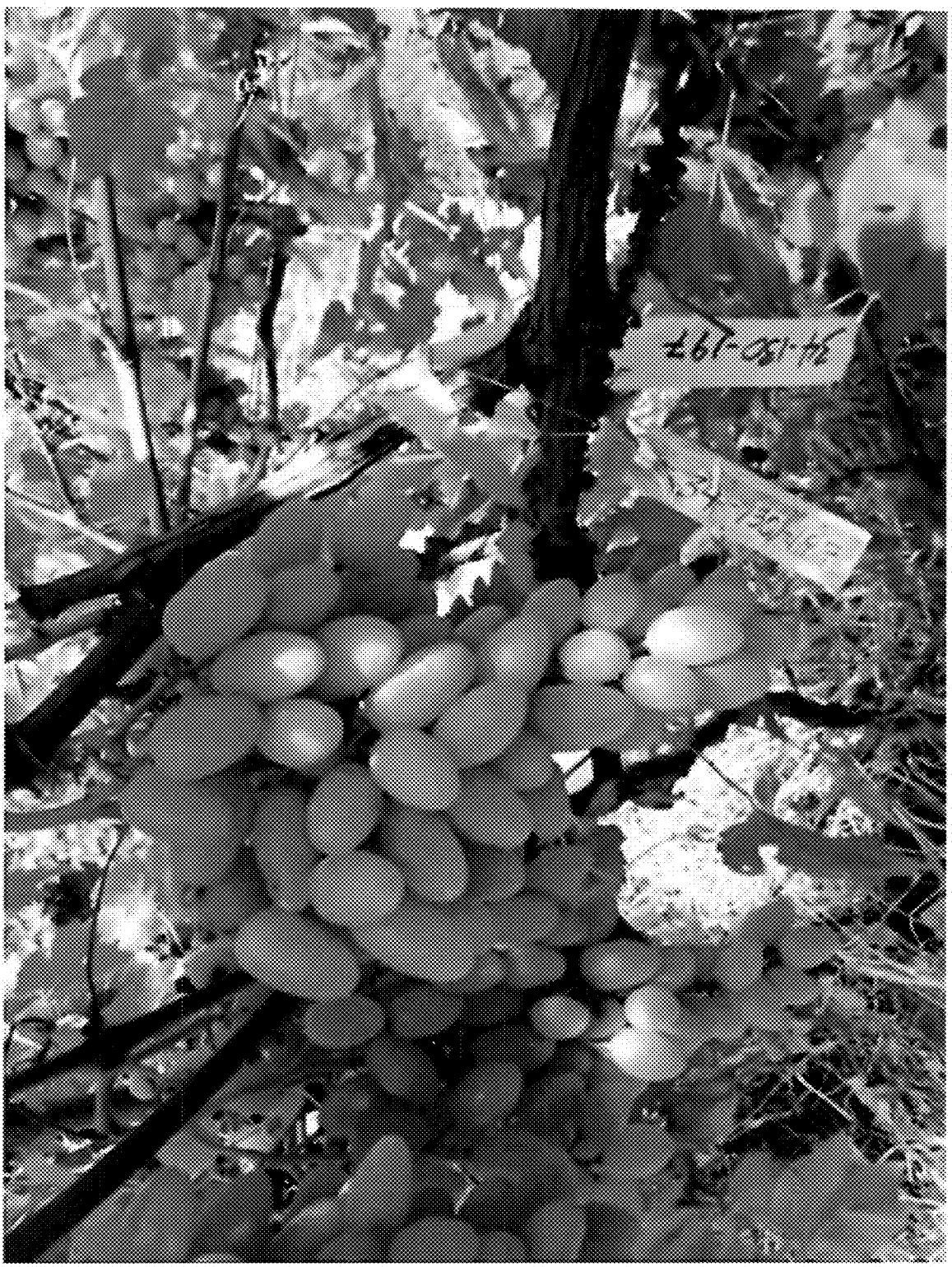
FIG. 1 Seedling vine with fruit clusters.
Figure 2:
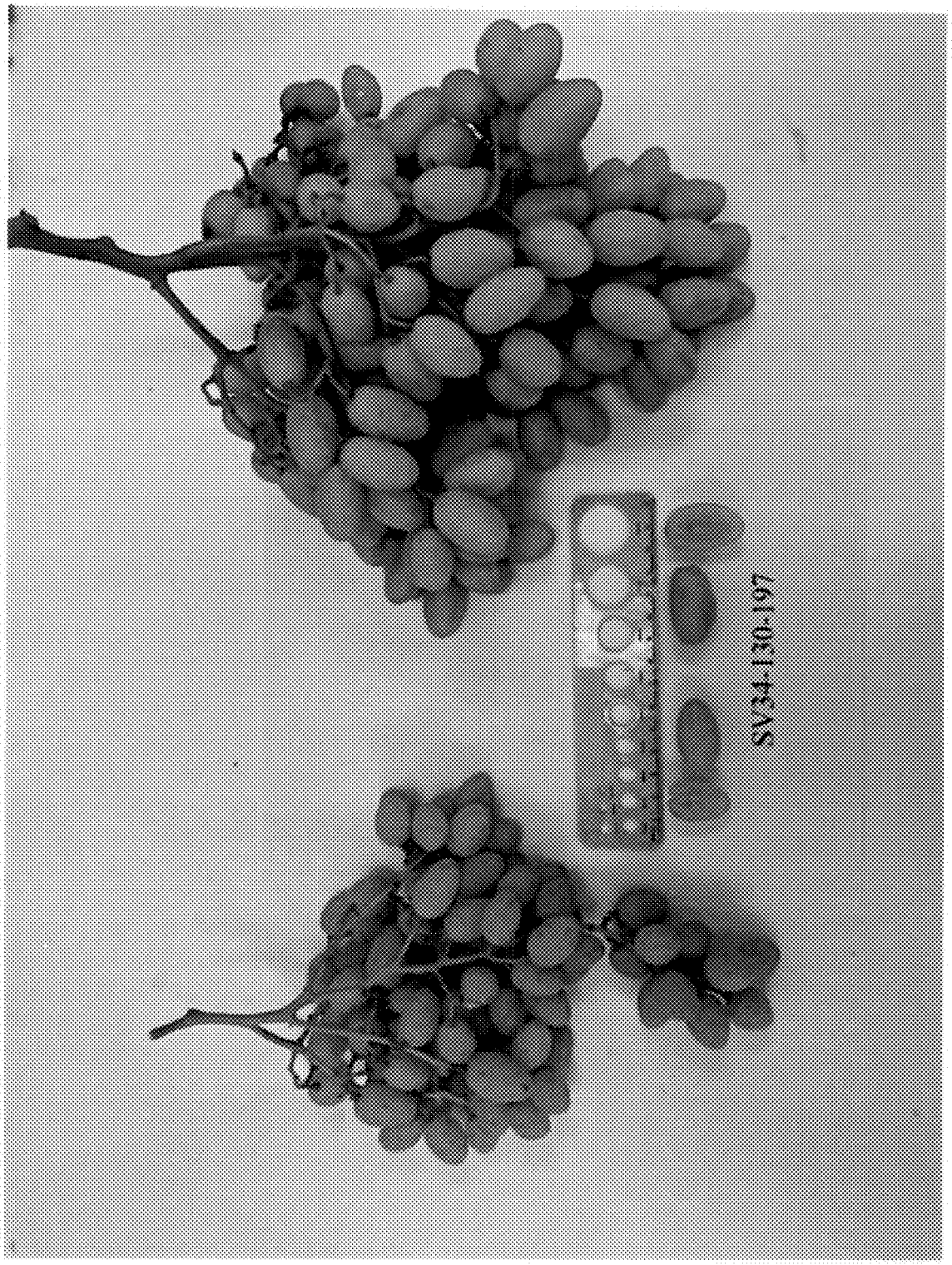
FIG. 2 Fruit cluster natural (at left) and fruit cluster treated with gibberellic acid and trunk girdling (at right).
Figure 3:
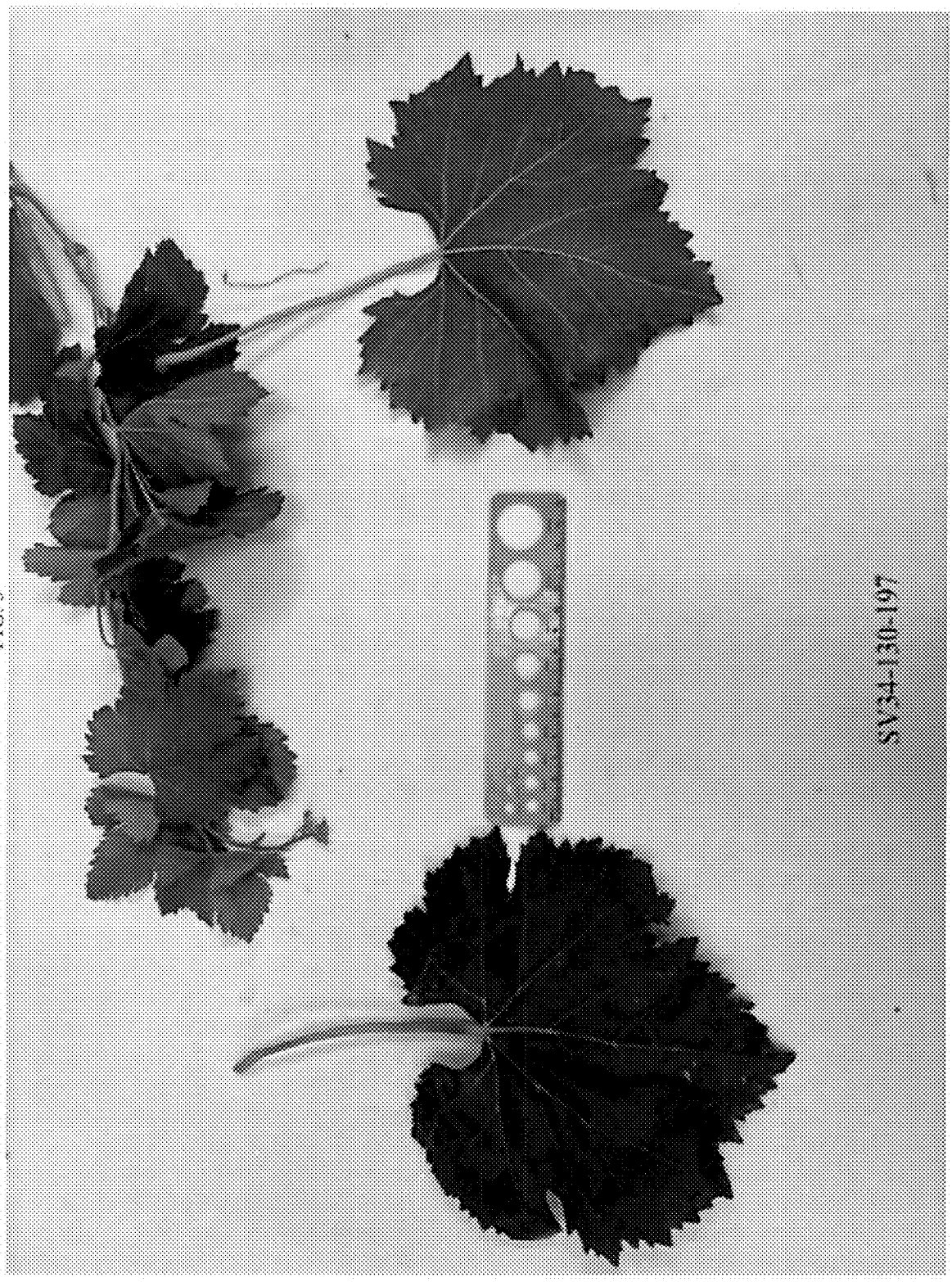
FIG. 3 Leaves and shoots.
Figure 4:
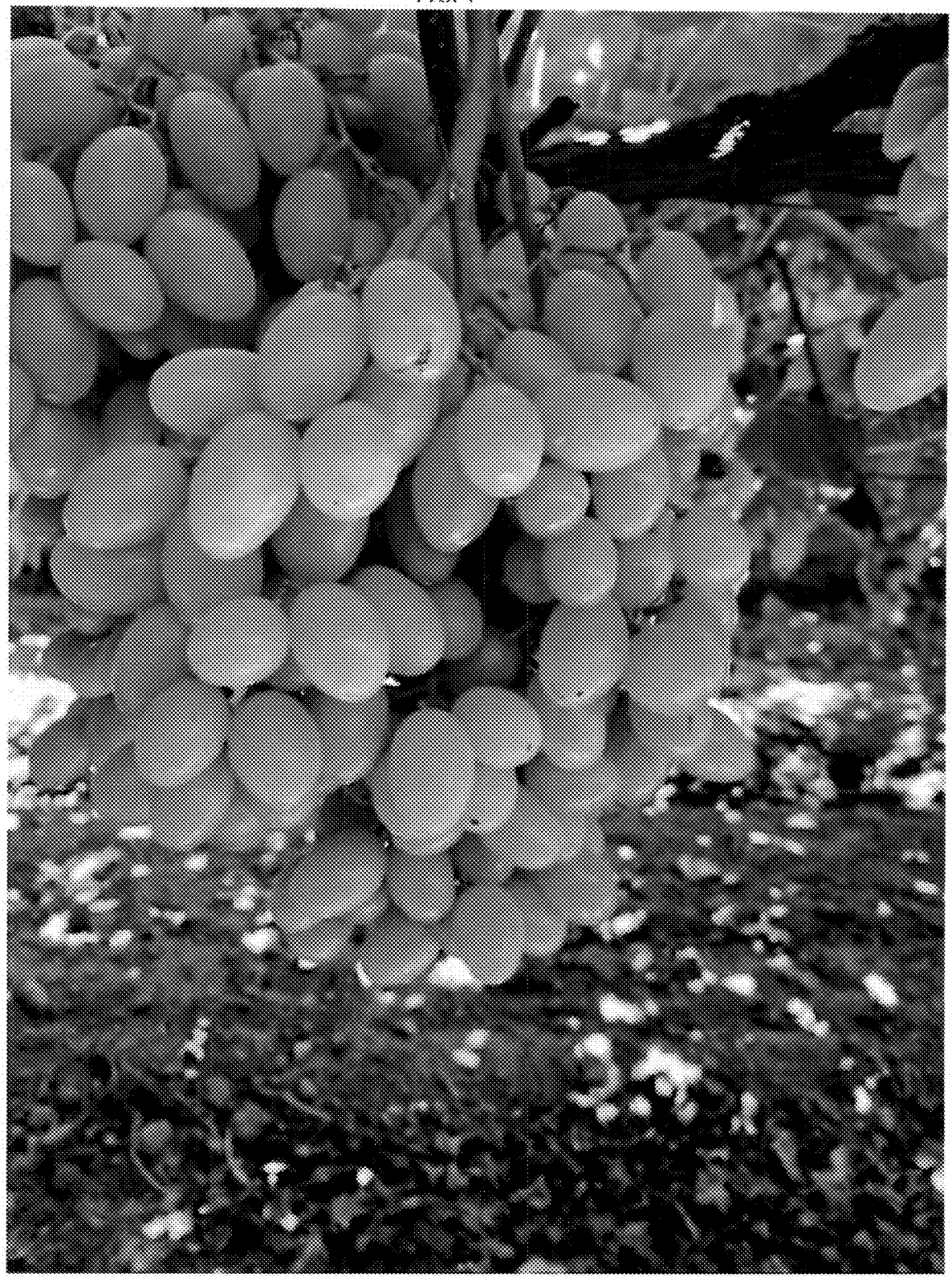
FIG. 4 Natural fruit cluster.
Figure 5:
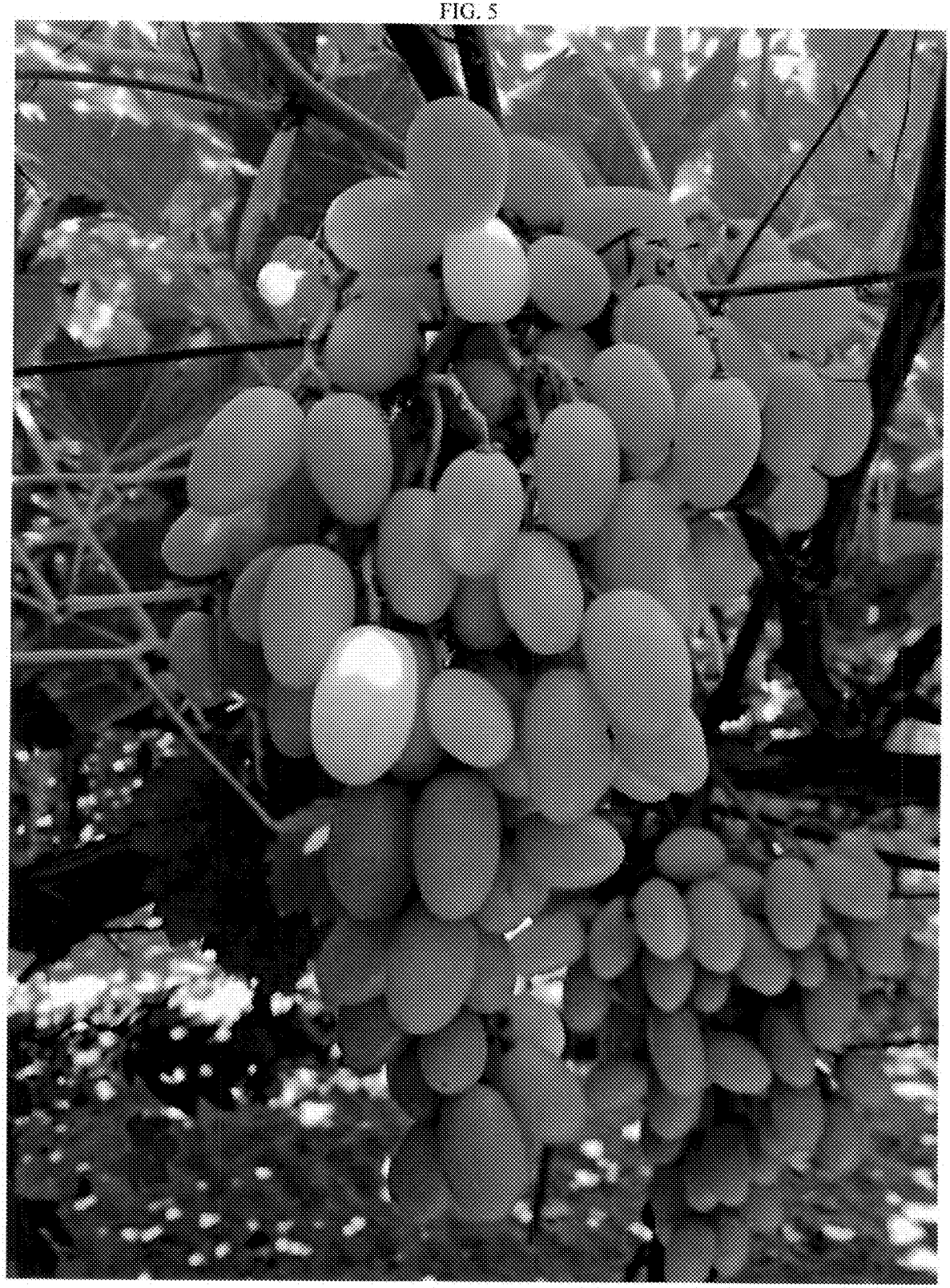
FIG. 5 Fruit cluster with exogenous gibberellic acid and trunk girdles applied.

The following detailed description sets forth the distinctive characteristics of grapevine named 'SV34-130-197'. Descriptions of the new invention apply to vines of grapevine 'SV34-130-197' grown on 'Freedom' (unpatented) rootstock at a density of 1,537 vines per hectare grown near McFarland, California in 2024. These vines were in their sixth year of production having been planted in 2017. These descriptions are believed to apply generally to the new variety grown under similar circumstances elsewhere. Variation due to soil and climatic conditions in other locations may be seen. References to color correspond to the Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis* spp.) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV34-130-197'.

Plant:

*Vigor*.—Vigorous; vines spur-pruned and shoot thinned to 32 shoots producing 209 cm of growth per cane.

*Density of foliage*.—Dense.

*Productivity*.—Very productive when spur pruned, up to 38,608 kg/hectare.

*Hardiness*.—Observed to 0 C.

*Rootstock*.—'Freedom' (unpatented).

*Bud Burst*.—Early.

Trunk:

*Shape*.—Broadly elliptical.

*Straps*.—Long, split.

*Surface texture*.—Shaggy.

*Trunk circumference*.—29.5 cm at 1.0 m of height.

*Inner bark color*.—RHS Greyed orange group 166B.

*Outer bark color*.—RHS Brown group 200A.

Mature leaves:

*Average blade length*.—16.5 cm.

*Average blade width*.—18.6 cm.

*Size of blade*.—Large.

*Shape*.—Pentagonal.

*Number of lobes*.—5.

*Anthocyanin coloration of main veins on the upper side of the blade*.—Absent.

*Mature leaf profile*.—Variable, some leaves undulating, some with leaf margins cupped downward and some leaves with margins cupped upwards.

*Blistering* (*upper surface*).—Absent.

*Leaf blade tip*.—Acuminate.

*Margins*.—Lobed, serrate, undulating.

*Apex*.—Broadly acuminate.

*Bases*.—Sagittate.

*Thickness*.—Medium.

*Undulation of blade between main and lateral veins*.—Slight.

*Shape of teeth*.—Conical, both sides convex.

*Length of teeth*.—9.6 mm.

*Width of teeth*.—10.8 mm.

*Ratio length/width of teeth*.—9.6:10.8.

*General shape of petiole sinus*.—Wide open.

*Tooth at petiole sinus*.—Absent.

*Petiole sinus limited by veins*.—Absent.

*Shape of upper lateral sinus*.—Open.

*Prostrate hairs between veins* (*lower surface*).—Absent.

*Erect hairs between veins* (*lower surface*).—Absent.

*Prostrate hairs on main veins* (*lower surface*).—Present.

*Density of erect hairs on main veins* (*lower surface*).—Medium density.

*Prostrate hairs on main veins* (*upper surface*).—Present.

*Upper surface*.—Summer color: RHS yellow-green 147A. Surface texture: Smooth. Surface appearance: Dull. Goffering of blade: Absent.

*Lower surface*.—Summer color: RHS green 137C. Anthocyanin coloration of main veins on lower leaf surface: Absent. Anthocyanin coloration on laterals: Absent. Glossiness: Low. Pubescence: Absent. Surface texture: Rough. Surface appearance: Dull.

*Petiole*.—Length: 14.8 cm. Length of petiole compared to middle vein: About equal. Density of prostrate hairs: Absent. Density of erect hairs: Absent. Shape of base of petiole sinus: Wide open. Color: In shade: RHS yellow-green group 145A. In sun: RHS yellow-green group N144D.

Tendrils:

*Number and Pattern*.—Bifurcated and trifurcated; Continuous after 5th node.

*Length*.—28.2 cm.

*Diameter*.—3.4 mm.

*Texture*.—Smooth.

*Color*.—RHS yellow-green group N144A.

Growing tips (young shoot):

*Pubescence*.—Present, prostrate.

*Prostrate hairs on tips of young shoots*.—Medium.

*Color*.—RHS yellow-green group 144A.

*Anthocyanins*.—Absent.

*Shape*.—Rounded.

*Apex*.—Fully open.

*Shoot attitude*.—Semi-erect.

Green summer shoots:

*Internode color upper surface*.—RHS yellow-green group 152B.

*Internode color lower surface*.—RHS yellow-green group 144B.

*Node color upper surface*.—RHS yellow-green group 152A.

*Node color lower surface*.—RHS yellow-green group 145A.
*Density of erect hairs on internodes*.—Absent.
*Internode length*.—10.7 cm.
*Width at node*.—14.5 mm.

Woody shoot:
*Canes*: Shape: Broadly elliptical. Internode length: About 12.5 cm. Width at node: 14.3 mm. Surface: Smooth. Main color: RHS Greyed Orange group 165B. Lenticels: Inconspicuous.
*Buds*.—Shape: Conical. Cane bud fruitfulness: Basal buds fruitful, 1 or 2 clusters per shoot. Length: 5.6 mm. Width: 3.0 mm. Height: 3.7 mm. Color: RHS Greyed orange group 166A.

Flowers:
*Flower sex*.—Hermaphrodite.
*Position of first flowering nodes*—4th node.
*Number of inflorescences per shoot*.—1 or 2.
*Flower cluster width*.—7.8 cm.
*Flower cluster length*.—34.8 cm.
*Cluster stem color*.—RHS Yellow green group 144B.
*Calyptra color*.—RHS Green group 143C.
*Ovary length* (*mm*).—3 mm.
*Ovary width* (*mm*).—1 mm.
*Ovary color*.—RHS yellow-green group 144B.
*Filament length*.—3 mm.
*Filament color*.—RHS Yellow green group 145C.
*Anther length* (*mm*).—1 mm.
*Anther color*.—RHS Yellow group 3C.
*Date of full bloom*.—May 2, 2024.

Fruit:
*Ripening period*.—Early season at McFarland, California.
*Date of ripening*.—Jul. 12, 2022 at McFarland, California.
*Use*.—Fresh market.
*Keeping quality*.—Very good.
*Shipping quality*.—Very good.
*Solids-sugar*.—17.5 brix at full maturity.
*Total acidity*.—0.74.
*pH*.—3.62.
*Bunch*.—Size: Large. Length (peduncle excluded): About 26.6 cm. Width: About 19.0 cm. Weight: Natural, without gibberellic acid treatment: 1055 g. With gibberellic acid treatment: 875 g. Density: Well filled, medium density. Number of berries: Natural: 192. Gibberellic acid treated: 189. Form: Conical
*Peduncle*.—Length: About 4.4 cm. Lignification: Slight, 0.5 cm. Color: RHS Yellow green group 144A.
*Berry*.—Size: Large. Uniformity of size: Somewhat uniform. Weight Natural, without gibberellic acid treatment: 4.4 g. With gibberellic acid treatment: 5.3 g. Shape: Natural, without gibberellic acid treatment: Narrow elliptic. With gibberellic acid treatment: Narrow elliptic. Presence of seeds: Seedless; most berries develop one or two small, soft rudimentary seeds less than 1.0 mm in length. Cross section: Circular. Dimensions: Natural: Longitudinal axis: About 2.8 cm. Horizontal axis: About 1.6 cm. With gibberellic acid application: Longitudinal axis: 3.0 cm. Horizontal axis: 1.7 cm. Skin color (without bloom): RHS Yellow Green group 151B. Coloration of flesh: RHS Yellow Green group 148D. Juiciness of flesh: Slightly juicy. Berry firmness: Firm. Particular flavor: Muscat. Bloom (cuticular wax): Medium. Pedicel length: 8.9 mm. Berry separation from pedicel: With difficulty; vascular traces well-developed.
*Skin*.—Thickness: Medium. Texture: Crisp. Reticulation: Absent. Roughness: Absent. Tenacity: Very tenacious to flesh. Tendency to crack: Resistant.

Disease and Insect Resistance: Grapevine plant named 'SV34-130-197' is known to be susceptible to powdery mildew of grapevine, *Erysiphe necator* Schwein. Standard commercial control measures for powdery mildew are adequate for complete control of this disease. No other diseases or insect pests have been observed on this grapevine plant named 'SV34-130-197'.

Having thus described and illustrated our new variety of grapevine, I claim:

1. A new and distinct variety of grapevine plant named 'SV34-130-197', substantially as illustrated and described herein.

* * * * *